(12) United States Patent
Jimenez et al.

(10) Patent No.: US 7,589,214 B2
(45) Date of Patent: Sep. 15, 2009

(54) THIAZOLES, IMIDAZOLES, AND PYRAZOLES USEFUL AS INHIBITORS OF PROTEIN KINASES

(75) Inventors: Juan-Miguel Jimenez, Abingdon (GB);
Ronald Knegtel, Abingdon (GB);
Daniel Robinson, Abingdon (GB);
Philip Collier, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 41 days.

(21) Appl. No.: 11/786,464

(22) Filed: Apr. 11, 2007

(65) Prior Publication Data
US 2007/0298065 A1    Dec. 27, 2007

Related U.S. Application Data

(60) Provisional application No. 60/791,083, filed on Apr. 11, 2006.

(51) Int. Cl.
C07D 233/64 (2006.01)
A61K 31/4164 (2006.01)
(52) U.S. Cl. .................... 548/300.1; 514/400
(58) Field of Classification Search ............... 548/300.1
See application file for complete search history.

(56) References Cited

U.S. PATENT DOCUMENTS 6,288,061 B1 * 9/2001 Sueoka et al. ............ 514/235.8

2004/0063671 A1 * 4/2004 Arrhenius et al. ........... 514/114

FOREIGN PATENT DOCUMENTS

WO   WO 2005012256 A1   2/2005
WO   WO 2006082309 A1   8/2006

OTHER PUBLICATIONS

International Search Report Received in the corresponding PCT Application No. PCT/US2007/008819.
Tosco, et al., "Furoxan analogues of the histamine H3-receptor antagonist imoproxifan and related furazan derivatives", Bioorganic & Medicinal Chemistry (2005), vol. 13, pp. 4750-4759.
Parang, et al., "Recent advances in the discovery of Src kinase inhibitors", Expert Opinion on Therapeutic Patients (2005), vol. 15, No. 9, pp. 1183-1207.
Coish, et al., "Small molecule inhibitors of IKK kinase activity", Expert Opinion on Therapeutic Patients (2006), vol. 16, No. 1, pp. 1-12.

* cited by examiner

*Primary Examiner*—Kamal A Saeed
*Assistant Examiner*—Shawquia Young
(74) *Attorney, Agent, or Firm*—Lisa A. Dixon; Booyong Shim Lim

(57) ABSTRACT

The present invention relates to compounds useful as inhibitors of protein kinase. The invention also relates to pharmaceutically acceptable compositions comprising the compounds, to methods of using the compounds and to the compositions in the treatment of various disease, conditions, or disorders. The invention also relates to processes for preparing compounds of the inventions.

19 Claims, No Drawings

THIAZOLES, IMIDAZOLES, AND PYRAZOLES USEFUL AS INHIBITORS OF PROTEIN KINASES

CROSS REFERENCE TO RELATED APPLICATIONS

This present application claims the benefit, under 35 U.S.C. §119, to U.S. Provisional Application No. 60/791,083, filed Apr. 11, 2006; the entire disclosure of which is incorporated herein by reference.

TECHNICAL FIELD OF THE INVENTION

The present invention relates to compounds useful as inhibitors of protein kinases. The invention also relates to pharmaceutically acceptable compositions comprising the compounds of the invention and methods of using the compositions in the treatment of various disorders. The invention also relates to processes for preparing the compounds of the invention.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. The Protein Kinase Facts Book, I and II, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., FASEB J. 1995, 9, 576-596; Knighton et al., Science 1991, 253, 407-414; Hiles et al., Cell 1992, 70, 419-429; Kunz et al., Cell 1993, 73, 585-596; Garcia-Bustos et al., EMBO J. 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

One kinase family of particular interest is the Src family of kinases. These kinases are implicated in cancer, immune system dysfunction and bone remodeling diseases. For general reviews, see Thomas and Brugge, Annu. Rev. Cell Dev. Biol. 1997, 13, 513; Lawrence and Niu, Pharmacol. Ther. 1998, 77, 81; Tatosyan and Mizenina, Biochemistry (Moscow) 2000, 65, 49-58; Boschelli et al., Drugs of the Future 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. Biochemistry (Moscow) 2000, 65, 49-58.

Based on published studies, Src kinases are considered as potential therapeutic targets for various human diseases. Mice that are deficient in Src develop osteopetrosis, or bone build-up, because of depressed bone resorption by osteoclasts. This suggests that osteoporosis resulting from abnormally high bone resorption can be treated by inhibiting Src. Soriano et al., Cell 1992, 69, 551 and Soriano et al., Cell 1991, 64, 693.

Suppression of arthritic bone destruction has been achieved by the overexpression of CSK in rheumatoid synoviocytes and osteoclasts. Takayanagi et al., J. Clin. Invest. 1999, 104, 137. CSK, or C-terminal Src kinase, phosphorylates and thereby inhibits Src catalytic activity. This implies that Src inhibition may prevent joint destruction that is characteristic in patients suffering from rheumatoid arthritis. Boschelli et al., Drugs of the Future 2000, 25(7), 717.

Src also plays a role in the replication of hepatitis B virus. The virally encoded transcription factor HBx activates Src in a step required for propagation of the virus. Klein et al., EMBO J. 1999, 18, 5019, and Klein et al., Mol. Cell. Biol. 1997, 17, 6427.

A number of studies have linked Src expression to cancers such as colon, breast, hepatic and pancreatic cancer, certain B-cell leukemias and lymphomas. Talamonti et al., J. Clin. Invest. 1993, 91, 53; Lutz et al., Biochem. Biophys. Res. 1998 243, 503; Rosen et al., J. Biol. Chem. 1986, 261, 13754; Bolen et al., Proc. Natl. Acad. Sci. USA 1987, 84, 2251; Masaki et al., Hepatology 1998, 27, 1257; Biscardi et al., Adv. Cancer Res. 1999, 76, 61; Lynch et al., Leukemia 1993, 7, 1416. Furthermore, antisense Src expressed in ovarian and colon tumor cells has been shown to inhibit tumor growth. Wiener et al., Clin. Cancer Res., 1999, 5, 2164; Staley et al., Cell Growth Diff. 1997, 8, 269.

Other Src family kinases are also potential therapeutic targets. Lck plays a role in T-cell signaling. Mice that lack the Lck gene have a poor ability to develop thymocytes. T-cells lacking Lck are shown to be severely impaired in TCR tyrosine phosphorylation and subsequent activation via the TCR. Straus et al., Cell 1992, 70, 585; Chan et al., Ann. Rev.

Immunol. 1994, 12, 555; Weiss et al., Cell 1994, 76, 263; Hanke et al., J. Biol. Chem. 1996, 271, 695; Van Oers at al., Immunity 1996, 5, 429. The function of Lck as a positive activator of T-cell signaling suggests that Lck inhibitors may be useful for treating of T cell mediated disorders such as autoimmune and inflammatory diseases and in the prevention of solid organ transplant rejection. Molina et al., Nature, 1992, 357, 161; Hanke et al., Inflammation Res. 1995, 44, 357. Hck, Fgr and Lyn have been identified as important mediators of integrin signaling in myeloid leukocytes. Lowell et al., J. Leukoc. Biol., 1999, 65, 313. Inhibition of these kinase mediators may therefore be useful for treating inflammation. Boschelli et al., Drugs of the Future 2000, 25(7), 717.

SUMMARY OF THE INVENTION

Compounds of this invention, and pharmaceutically acceptable compositions thereof, are useful as inhibitors of protein kinases. In some embodiments, these compounds are effective as inhibitors of Src family protein kinases; in some embodiments, as inhibitors of Lck protein kinases. These compounds have the formula I, as defined herein, or a pharmaceutically acceptable salt thereof.

These compounds and pharmaceutically acceptable compositions thereof are useful for treating or preventing a variety of diseases, disorders or conditions, including, but not limited to, an autoimmune, inflammatory, proliferative, or hyperproliferative disease, an immunologically-mediated disease, or bone disease. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention provides compounds of Formula I:

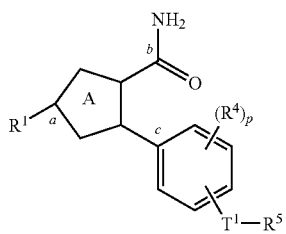

or a pharmaceutically acceptable salt thereof;
wherein
$R^1$ is a 3-7 membered monocyclic cycloalkyl optionally substituted with 0-4 $J^1$;
Ring

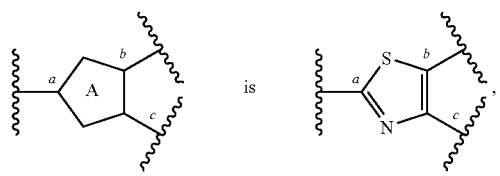 is

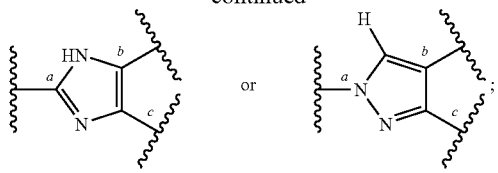

$R^4$ is H, $C_{1-6}$aliphatic, $C_{3-6}$cycloaliphatic, halo($C_{1-4}$ aliphatic), 3-8 membered heterocyclyl, halo, $NO_2$, CN, OH, OR", SH, SR", $NH_2$, N(H)R", N(R")$_2$, COH, COR", $CO_2$H, $CO_2$R", C(O)NH$_2$, C(O)NHR", C(O)NR"$_2$, OC(O)R", OC(O)NH$_2$, OC(O)NHR", OC(O)N(R")$_2$, N(H)C(O)R", N(R")C(O)R", N(H)CO$_2$R", N(R")CO$_2$R", N(H)CO$_2$H, N(R")CO$_2$H, N(H)CONH$_2$, N(H)C(O)N(H)R", N(H)C(O)N(R")$_2$, SO$_2$NH$_2$, SO$_2$N(H)R", SO$_2$N(R")$_2$, N(H)SO$_2$R", N(R")SO$_2$R", P(O)R', P(O$_2$)R', P(O)R'$_2$, or P(O)OR'$_2$;

R" is unsubstituted $C_{1-6}$aliphatic or $C_{1-4}$ haloaliphatic; or two R" groups, together with the atom to which they are bound, form an unsubstituted 3-8 membered nonaromatic monocyclic ring having 0-1 heteroatoms independently selected from O, N, and S;

$T^1$ is a $C_{1-6}$ aliphatic chain wherein 0-3 methylene units of the chain are optionally replaced with —NR—, —O—, —S—, —C(O)—, —C(=NR)—, —C(=NOR)—, —SO—, or —SO$_2$—; each $T^1$ is optionally substituted with 0-2 $J^T$;

$R^5$ is a 5-10 membered aromatic ring containing 0-4 heteroatoms selected from O, N, and S; each $R^5$ is optionally substituted with 0-5 $J^5$;

$J^5$ is H, $C_{1-6}$ aliphatic, $C_{3-8}$cycloaliphatic, halo($C_{1-4}$ aliphatic), 3-8 membered heterocyclyl, halo, $NO_2$, CN, OH, OR', SH, SR', $NH_2$, NHR', N(R')$_2$, C(O)H, C(O)R', $CO_2$H, $CO_2$R', C(O)NH$_2$, C(O)N(H)R', C(O)NR'$_2$, OC(O)R', OC(O)NH$_2$, OC(O)N(H)R', OC(O)NR'$_2$, N(H)C(O)R', N(R')C(O)R', N(H)CO$_2$R', N(R')CO$_2$R', N(H)CO$_2$H, N(R')CO$_2$H, N(H)CONH$_2$, N(H)C(O)N(H)R', N(H)C(O)NR'$_2$, SO$_2$NH$_2$, SO$_2$N(H)R', SO$_2$NR'$_2$, N(H)SO$_2$R', N(R')SO$_2$R', P(O)R', PO$_2$R', P(O)R'$_2$, or P(O) (OR')$_2$;

R is H or unsubstituted $C_{1-6}$aliphatic;
R' is unsubstituted $C_{1-6}$aliphatic or $C_{1-4}$ haloaliphatic; or two R' groups, together with the atom to which they are bound, form an unsubstituted 3-8 membered nonaromatic monocyclic ring having 0-1 heteroatoms independently selected from O, N, and S;

$J^1$ is $M^1$ or —$Y^1$-$M^1$;
each $Y^1$ is independently an unsubstituted $C_{1-6}$aliphatic optionally replaced with 0-3 occurrences of —NR—, —O—, —S—, —C(O)—, —SO—, or —SO$_2$—;

each $M^1$ is independently H, $C_{1-6}$ aliphatic, $C_{3-8}$cycloaliphatic, halo($C_{1-4}$ aliphatic), —O(halo$C_{1-4}$ aliphatic), 3-8 membered heterocyclyl, 5-6 membered heteroaryl, phenyl, halo, $NO_2$, CN, OH, OR', SH, SR', $NH_2$, N(H(R', N(R')$_2$, C(O)H, C(O)R', $CO_2$H, $CO_2$R', C(O)NH$_2$, C(O)N(H)R', C(O)NR'$_2$, OC(O)R', OC(O)NH$_2$, OC(O)N(H(R', OC(O)NR'$_2$, N(H)C(O)R', N(R')C(O)R', N(H)CO$_2$R', N(R')CO$_2$R', N(H)CO$_2$H, N(R')CO$_2$H, N(H)C(O)NH$_2$, N(H)C(O)N(H)R', N(H)C(O)NR'$_2$, SO$_2$NH$_2$, SO$_2$NHR', SO$_2$N(R')$_2$, NHSO$_2$R', NR'SO$_2$R', P(O)R', PO$_2$R', P(O)R'$_2$, or P(O)(OR')$_2$;

each $R^4$, $J^5$, and $M^1$ is independently and optionally substituted with 0-5 J;
each $J^T$ and J is independently H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), COH, —C(O)($C_{1-4}$ aliphatic), C(O)NH$_2$, C(O)N(H)($C_{1-4}$ aliphatic), C(O)N($C_{1-4}$ aliphatic)$_2$, —CO$_2$H, —CO$_2$($C_{1-4}$ aliphatic), —O(halo$C_{1-4}$ aliphatic), or halo($C_{1-4}$ aliphatic);

p is 0-4.

These compounds, and pharmaceutically acceptable compositions thereof, are useful for treating or lessening the severity of a variety of disorders including hypercalcemia, osteoporosis, osteoarthritis, cancer, symptomatic treatment of bone metastasis, Paget's disease, autoimmune diseases such as transplant rejection, allergies, rheumatoid arthritis, and leukemia.

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "heterocycle", "heterocyclyl", or "heterocyclic" as used herein means non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a heteroatom independently selected from oxygen, sulfur, nitrogen, or phosphorus, and each ring in the system contains 3 to 7 ring members.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Exemplary protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, the methylene units of an alkyl or aliphatic chain can be optionally replaced with another atom or group. Examples of such atoms or groups would include, but are not limited to, —NR—, —O—, —C(O)—, —C(=N—CN)—, —C(=NR)—, —C(=NOR)—, —S—, —SO—, or —SO$_2$—. These atoms or groups can be combined to form larger groups. Examples of such groups include, but are not limited to, —OC(O)—, —C(O)CO—, —CO$_2$—, —C(O)NR—, —C(=N—CN), —NRCO—, —NRC(O)O—, —SO$_2$NR—, —NRSO$_2$—, —NRC(O)NR—, —OC(O)NR—, and —NRSO$_2$NR—, wherein R is defined herein.

Unless otherwise specified, the optional replacements form a chemically stable compound. Optional replacements can occur both within the chain and at either end of the chain; i.e. both at the point of attachment and/or also at the terminal end. Two optional replacements can also be adjacent to each other within a chain so long as it results in a chemically stable compound.

The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise specified, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise stated, structures depicted herein are also meant to include all isomeric (e.g., enantiomeric, diastereomeric, geometric, conformational, and rotational forms of the structure). For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

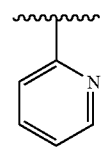

also represents

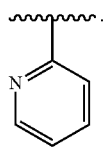

Therefore, single stereochemical isomers as well as enantiomeric, diastereomeric, geometric, conformational, or rotational mixtures of the present compounds are within the scope of the invention.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

It will also be appreciated that certain of the compounds of present invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

Base addition salts can be prepared by 1) reacting the purified compound in its acid form with a suitable organic or inorganic base and 2) isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

The following abbreviations are used:
DMSO dimethyl sulfoxide
DCM dichloromethane
THF tetrahydrofuran
ATP adenosine triphosphate
HEPES 4-(2-hydroxyethyl)-1-piperazineethanesulfonic acid
NMR nuclear magnetic resonance
HPLC high performance liquid chromatography
LCMS liquid chromatography-mass spectrometry
Rt retention time
TBABr$_3$ tetrabutylammonium tribromide One embodiment of this invention provides compounds of formula II:

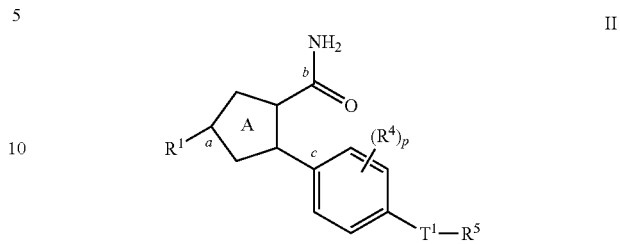

II wherein $R^1$, $R^4$, $T^5$, $T^1$, Ring A, and p are defined herein.

In one embodiment of this invention, $R^1$ is a 5 or 6 membered cycloalkyl ring. In another embodiment, $R^1$ is cyclopentyl. In yet another embodiment, $R^1$ is cyclohexyl.

In some embodiments, Ring

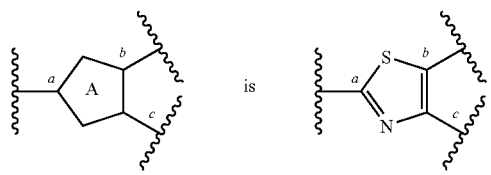

In other embodiments, Ring

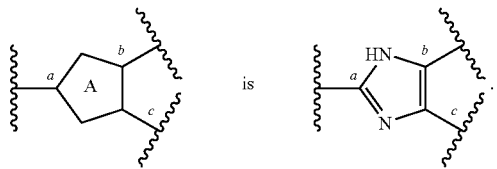

In yet other embodiments, Ring

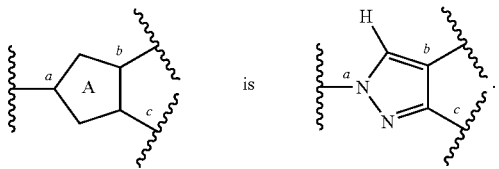

In some embodiments, Ring

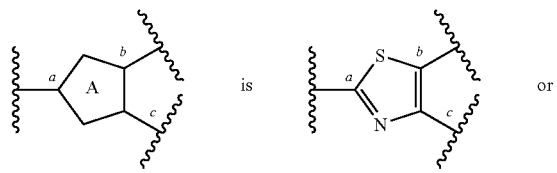

-continued

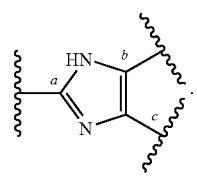

In some embodiments of the present invention, $R^4$ is H, halo, $C_{1-6}$ aliphatic, $C_{3-6}$cycloaliphatic, $NO_2$, CN, $—NH_2$, $—NH(C_{1-4}$ aliphatic), $—N(C_{1-4}$ aliphatic)$_2$, $—OH$, $—O(C_{1-4}$ aliphatic), COH, $—CO(C_{1-4}$ aliphatic), $CONH_2$, $CONH(C_{1-4}$ aliphatic), $CON(C_{1-4}$ aliphatic)$_2$, $—CO_2H$, $—CO_2(C_{1-4}$ aliphatic), $—O(haloC_{1-4}$ aliphatic), or halo($C_{1-4}$ aliphatic).

In some embodiments, $T^1$ is O, N, S, —C(O)N(R)— or —N(R)C(O)—. In other embodiments, $T^1$ is O. In some embodiments, R is H.

In one embodiment of this invention, $R^5$ is an optionally substituted indole. In another embodiment, $R^5$ is an optionally substituted 6-membered aryl or heteroaryl ring. In some embodiments, $R^5$ is optionally substituted phenyl.

In some embodiments, $J^5$ is H, halo, $C_{1-6}$ aliphatic, $C_{3-6}$cycloaliphatic, $NO_2$, CN, $—NH_2$, $—NH(C_{1-4}$ aliphatic), $—N(C_{1-4}$ aliphatic)$_2$, $—OH$, $—O(C_{1-4}$ aliphatic), COH, $—CO(C_{1-4}$ aliphatic), $CONH_2$, $CONH(C_{1-4}$ aliphatic), $CON(C_{1-4}$ aliphatic)$_2$, $—CO_2H$, $—CO_2(C_{1-4}$ aliphatic), $—O(haloC_{1-4}$ aliphatic), or halo($C_{1-4}$ aliphatic).

For the avoidance of doubt, it should be understood that in a certain embodiment, p is 0, $T^1$ is O, $R^5$ is optionally substituted phenyl, and $R^1$ cyclopentyl or cyclohexyl.

In certain embodiments, the variables are defined as depicted in compounds I-1, I-2, I-3, and I-4.

One embodiment provides the following compounds:

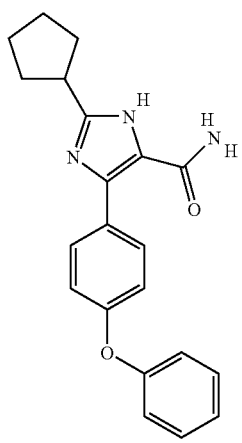

I-1

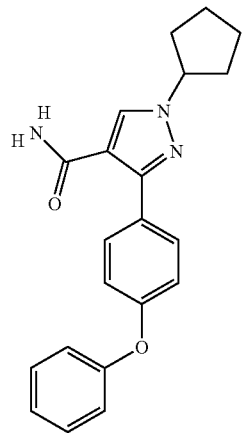

I-2

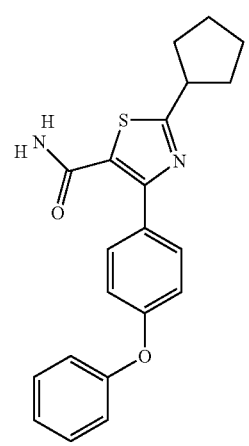

I-3

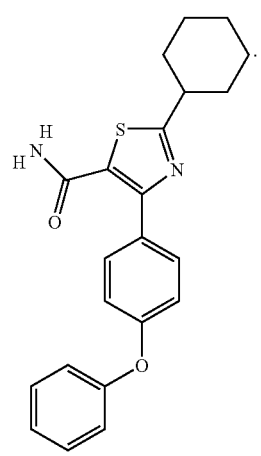

I-4

General Synthetic Methodology

The compounds of this invention may be prepared in general by methods such as those depicted in the general schemes below, and the preparative examples that follow. Unless otherwise specified, Ring A, $T^1$, $R^1$, $R^4$, $R^5$, $R^4$, and p are as defined herein.

Scheme 1

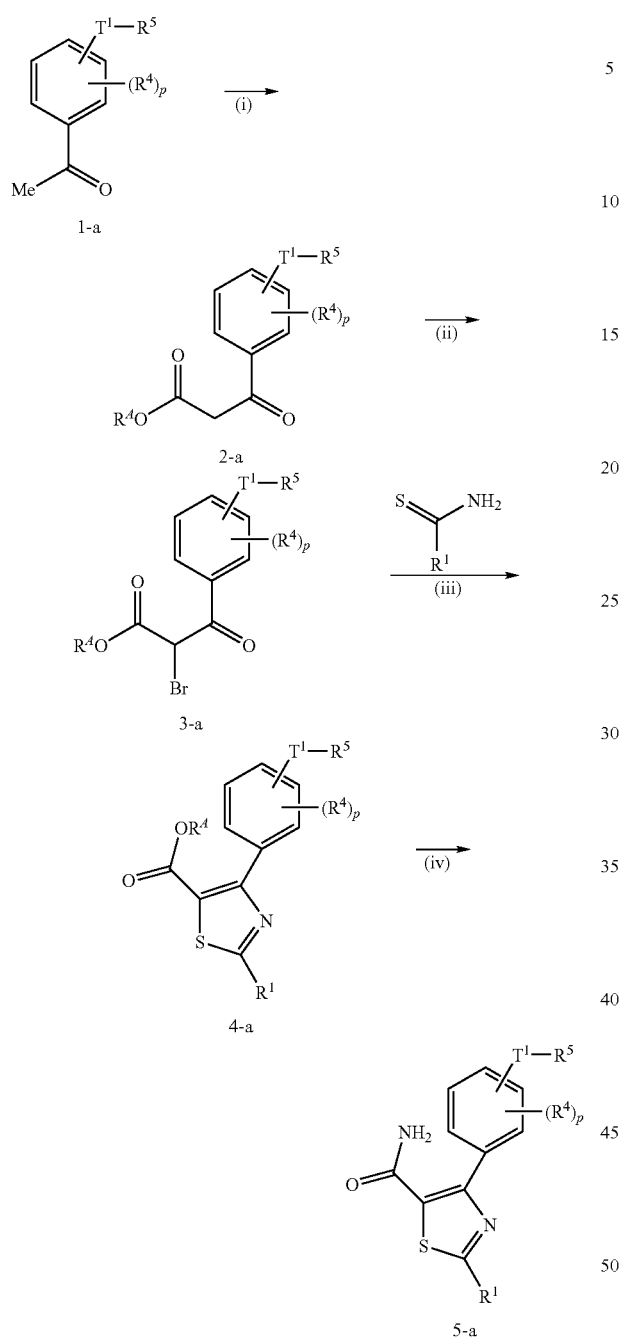

Reagents and conditions: (i) NaH then CO(OMe)$_2$, toluene, (ii) TBABr$_3$, CH$_2$Cl$_2$, reflux, (iii) EtOH, reflux, (iv) NH$_3$ in MeOH, sealed tube, 90° C.

Scheme 1 above shows a general synthetic route that is used for preparing the compounds 5-a (compounds of formula I wherein Ring A is thiazolyl and T$^1$, R$^1$, R$^4$, R$^5$, and p are as described herein). Compounds of formula 5-a can be prepared from intermediate 1-a. The formation of derivative 2-a is achieved by treating intermediate 1-a with a corresponding base and dimethyl carbonate. Bromination of 2-a using TBABr$_3$ leads to a formation of 3-a, which can be reacted with a corresponding thioamide to give 4-a. This reaction is amenable to a variety of thioamides derivatives R$^2$C(S)NH$_2$. The ester in 4-a can then be converted to an amide under suitable amide-formation conditions.

Scheme 2

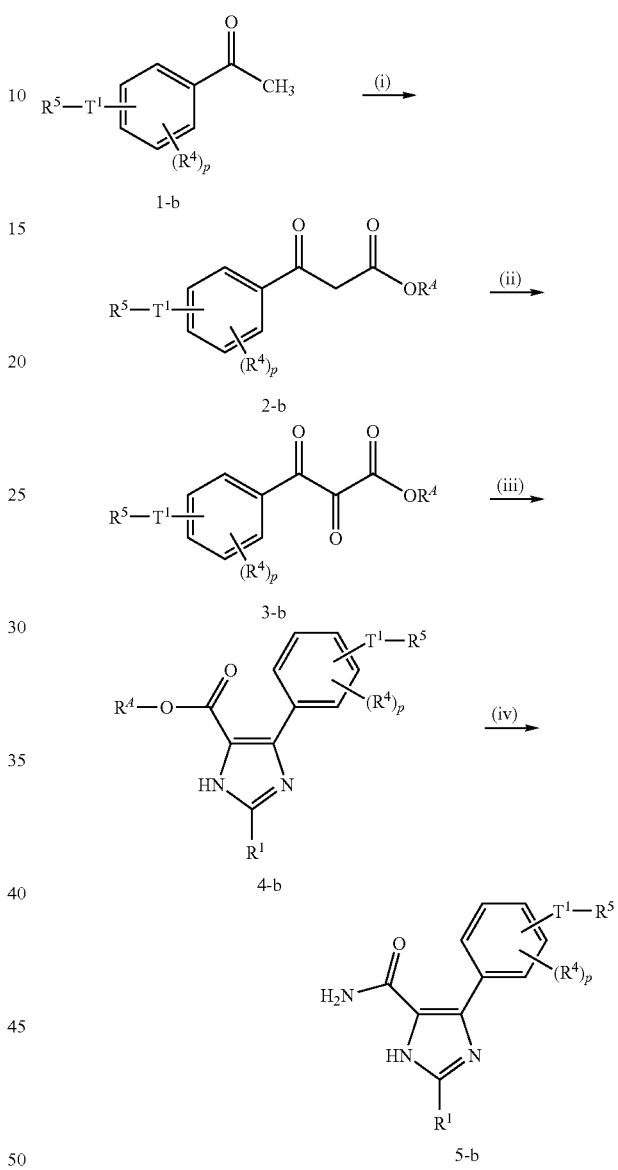

Reagents and conditions: (i) NaH, THF, reflux then EtO-COOEt, (ii) Dess-Martin periodinane, pyridine, DCM, (iii) R$^2$CHO, NH$_4$OAc, AcOH, 65° C. (iv) NH$_4$OH, MeOH, 80° C.

Scheme 2 above shows a general synthetic route that is used for preparing the compounds 5-b (compounds of formula I wherein Ring A is imidazolyl and T$^1$, R$^1$, R$^4$, R$^5$, and p are as described herein). Compounds of formula 5-b can be prepared from intermediates 1-b. The formation of derivatives 2-b is achieved by treating the intermediate 1-b with a base and diethylcarbonate. Reaction of 2-b with Dess-Martin periodinane followed by cyclisation with an aldehyde R$^1$CHO gives intermediates 4-b. The reaction is amenable to a variety of aldehydes R$^1$CHO. Finally, derivatives 5-b were prepared according to step (iv) of Scheme 1.

Compound I-1 was prepared as shown in Scheme 2.

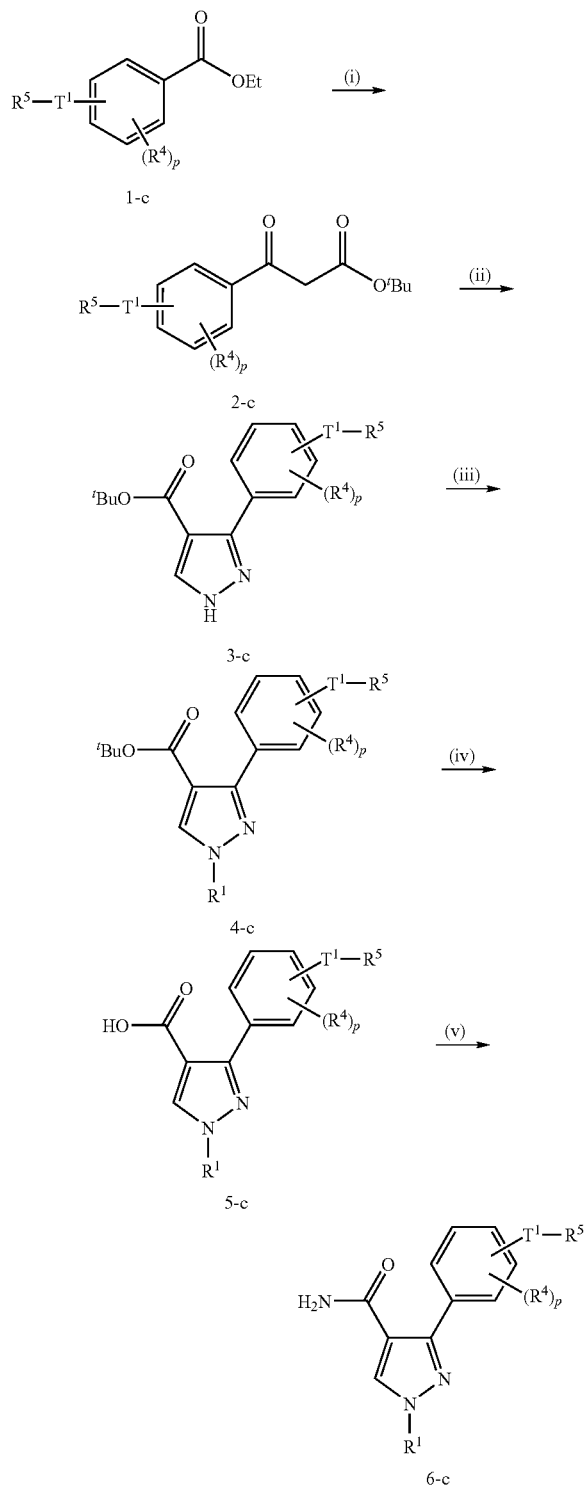

Reagents and conditions: (i) LDA, THF then MeCOO$^t$Bu, (ii) a) Bredereck's reagent, THF, reflux, b) H$_2$NNH$_2$.H$_2$O, EtOH, reflux, (iii) R$^2$X, NaH, DMF, (iv) TFA, DCM, (v) COIm$_2$, DMF, then NH$_{3gas}$.

Scheme 3 above shows a general synthetic route that is used for preparing the compounds 6-c (compounds of formula I wherein Ring A is pyrazolyl and T$^1$, R$^1$, R$^4$, R$^5$, and p are as described herein). Compounds of formula 6-c can be prepared from intermediates 1-c. The formation of derivatives 2-c is achieved by treating the intermediate 1-c with a base and tert-butylacetate. Reaction of 2-c with Bredereck's reagent followed by cyclisation with hydrazine gives intermediates 3-c, which can be alkylated with an alkylhalide R$^1$X to give compounds of formula 4-c. The reaction is amenable to a variety of alkylhalides R$^1$X. Saponification of tert-butyl esters 4-c leads to compounds 5-c. Finally, derivatives 6-c were prepared according to step (iv) of Scheme 1.

Accordingly, the present invention also provides processes for making the compounds of this invention.

One embodiment of this invention provides a process for preparing a compound of formula I:

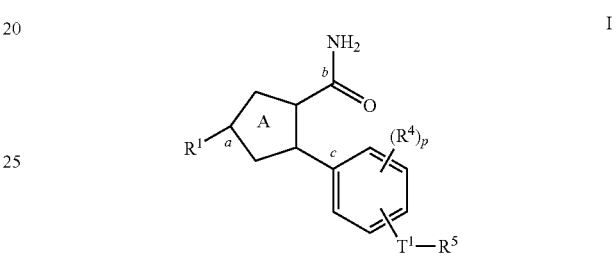

wherein ring

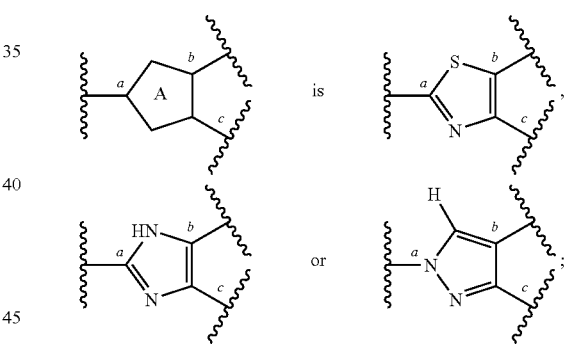

and R$^1$, R$^4$, T$^1$, R$^5$, and p are defined herein;

comprising reacting a compound of formula 4;

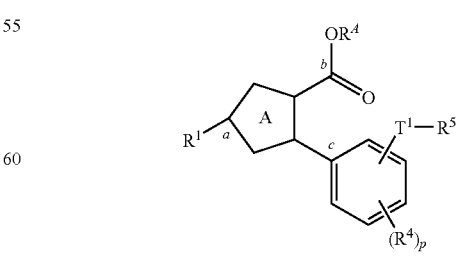

wherein Ring A, R$^1$, R$^4$, T$^1$, R$^5$, and p are defined herein and R$^4$ is H or C$_{1-6}$alkyl;

under suitable amide-formation conditions to form the compound of formula I. Suitable amide formation conditions include, but are not limited to, heating an ester with ammonia/MeOH, activating a carboxylic acid with an activating agent, such as carbonyl diimidazole, and then stirring the activated acid in the presence of ammonia gas. In some embodiments, when Ring A is thiazolyl or imidazolyl, $R^A$ is $C_{1-6}$alkyl. When Ring A is pyrazolyl, $R^A$ is H.

Another embodiment comprises the step of reacting a compound of formula 3-a:

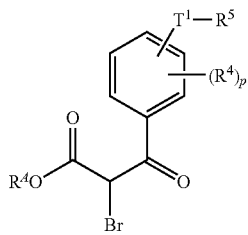

3-a wherein $T^1$, $R^4$, $R^5$, and p are defined herein;

with

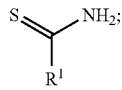

wherein $R^1$ is as defined herein;

under suitable displacement and cyclization conditions to form a compound of formula 4-a (a compound of formula 4 wherein ring

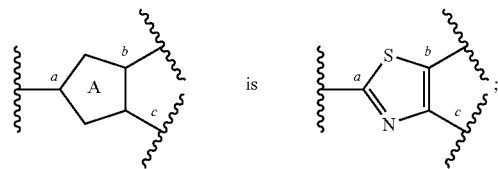

$R^A$ is $C_{1-6}$alkyl; and $R^1$, $R^4$, $T^1$, $R^5$, and p are defined according to claim 1):

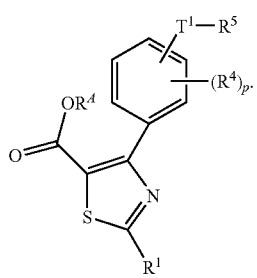

4-a

Suitable displacement and cyclization conditions include heating the thioamide and the ketoester in a suitable solvent, such as, for example, ethanol.

Another embodiment comprises the step of reacting a compound of formula 2-a:

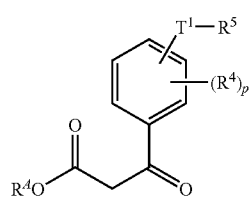

2-a wherein $T^1$, $R^4$, $R^5$, and p are defined herein; and $R^A$ is $C_{1-6}$alkyl;

with a halogenating agent (e.g., tetrabutyl ammonium tribromide) to form a compound of formula 3-a.

Another embodiment comprises the step of mixing a compound of formula 1-a:

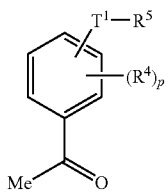

1-a wherein $T^1$, $R^4$, $R^5$, and p are defined herein;

with dimethylcarbonate and a base in a suitable solvent to form a compound of formula 2-a. Examples of bases include, but are not limited to, NaH. Examples of suitable solvents include, but are not limited to, toluene. In some embodiments, acetic acid is used to quench the reaction.

Another embodiment comprises the steps of:
a) reacting a compound of formula 2-b;

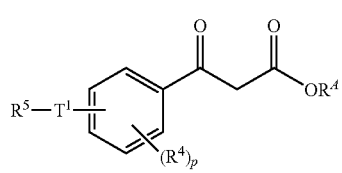

2-b wherein $R^4$, $T^1$, $R^5$, and p are defined herein; and $R^A$ is $C_{1-6}$alkyl;

under suitable oxidizing conditions to form a compound of formula 3-b:

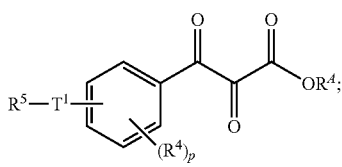

3-b wherein $R^4$, $T^1$, $R^5$, and p are defined herein; and $R^A$ is $C_{1-6}$alkyl;

and b) cyclizing the compound of formula 3-b with $R^1$CHO under suitable cyclization conditions to form a compound of formula 4-b (A compound of formula 4 wherein ring

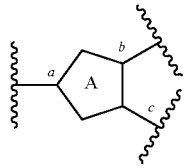 is 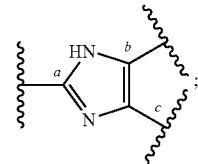 ;

$R^A$ is $C_{1-6}$alkyl, and $R^1$, $R^4$, $T^1$, $R^5$, and p are defined according to claim 1):

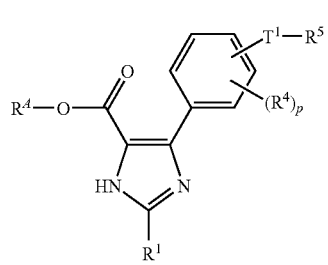

4-b wherein $R^1$, $R^4$, $T^1$, $R^5$, and p are defined herein; and $R^A$ is $C_{1-6}$alkyl.

Suitable cyclization conditions include, but are not limited to, NH$_4$OAc and AcOH at 65° C. Suitable oxidizing conditions include, but are not limited to, treatment with Dess-Martin periodinane.

One embodiment comprises the step of reacting a compound of formula 1-b:

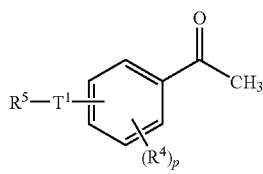

1-b wherein $R^4$, $T^1$, $R^5$, and p are defined herein;

with a suitable base and diethylcarbonate under suitable conditions; to form a compound of formula 2-b.

Another embodiment comprises the step of reacting a compound of formula 4-c (A compound of formula 4 wherein ring

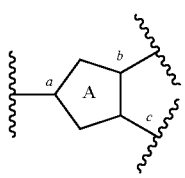 is 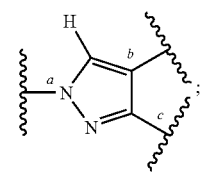 ;

$R^A$ is t-Butyl, and $R^1$, $R^4$, $T^1$, $R^5$, and p are defined according to claim 1):

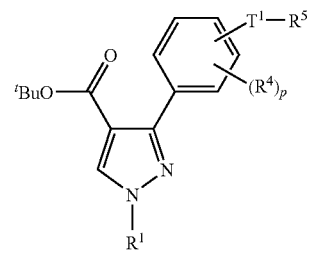

4-c under suitable saponification conditions to form a compound of formula 5-c:

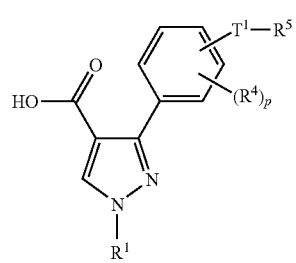

5-c wherein $R^1$, $R^4$, $T^1$, $R^5$, and p are defined herein. Suitable saponification conditions include, but are not limited to, stirring the compound in the presence of an acid (e.g., trifluoroacetic acid) and a solvent (e.g., CH$_2$Cl$_2$).

Yet another embodiment comprises the step of reacting a compound of formula 3-c:

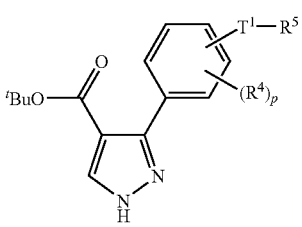

3-c wherein $R^4$, $T^1$, $R^5$, and p are defined herein;

with a suitable base (e.g., NaH) and an alkylhalide $R^1$X, wherein X is a halo selected from F, Br, and I and $R^1$ is defined according to claim 1; to form a compound of formula 4-c wherein $R^1$, $R^4$, $T^1$, $R^5$, and p are defined herein.

Yet another embodiment comprises the steps of
a) reacting a compound of formula 2-c:

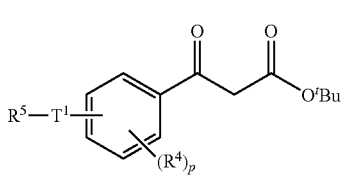

2-c wherein $R^4$, $T^1$, $R^5$, and p are defined herein;

with Bredereck's reagent; and b) cyclizing the resulting compound with hydrazine to form a compound of formula 3-c; wherein $R^1$, $R^4$, $T^1$, $R^5$, and p are defined according to claim 1.

One embodiment comprises the step of reacting a compound of formula 1-c:

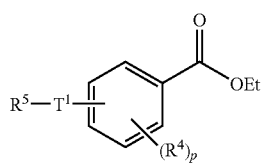

1-c wherein $R^4$, $T^1$, $R^5$, and p are defined herein;

with a suitable base (e.g., n-BuLi and diisopropyl ethylamine) and tert-butylacetate under suitable conditions (e.g., stirring in anhydrous THF at −78° C.) to form a compound of formula 2-c, wherein $R^4$, $T^1$, $R^5$, and p are defined herein.

Utility as Protein Kinase Inhibitors

The present invention provides compounds and compositions that are useful as inhibitors of protein kinases. In some embodiments, protein kinases are Src-family kinases. In some embodiments, Lck.

As inhibitors of protein kinases, the compounds and compositions of this invention are particularly useful for treating or lessening the severity of a disease, condition, or disorder where a protein kinase is implicated in the disease, condition, or disorder. In one aspect, the present invention provides a method for treating or lessening the severity of a disease, condition, or disorder where a protein kinase is implicated in the disease state. In another aspect, the present invention provides a method for treating or lessening the severity of a disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor.

In some embodiments, said protein kinase inhibitor is an Src-family kinase inhibitor. In some embodiment, said protein kinase inhibitor is an LCK kinase inhibitor.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means a sample that is not an in vivo sample, such as an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of this invention provides compounds that are useful for the treatment of diseases, disorders, and conditions including, but not limited to, autoimmune diseases, inflammatory diseases, proliferative and hyperproliferative diseases, immunologically-mediated diseases, bone diseases, metabolic diseases, cardiovascular diseases, hormone related diseases, allergies, asthma, and Alzheimer's disease.

For example, the present invention provides compounds that are useful for treating diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additional diseases include, without limitation, those conditions characterised by inflammation of the nasal mucus membrane, including acute rhinitis, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

Another aspect of this invention provides compounds that are useful for treating diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

Another aspect of this invention provides compounds that are useful for treating diseases and disorders of other tissues and systemic disease, including, without limitation, multiple sclerosis, atherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), atherosclerosis, and systemic lupus erythematosus.

Another aspect of this invention provides compounds that are useful for allograft rejection, including, without limitation, acute and chronic allograft rejection following for example transplantation of kidney, heart, liver, lung, bone marrow, skin and cornea; and chronic graft versus host disease.

Another aspect of this invention provides a method for the treatment or lessening the severity of a disease selected from an autoimmune disease, an inflammatory disease, a proliferative or hyperproliferative disease, such as cancer, an immunologically-mediated disease, a bone disease, a metabolic disease, a neurological or neurodegenerative disease, a cardiovascular disease, allergies, asthma, Alzheimer's disease, or a hormone related disease, comprising administering an effective amount of a compound, or a pharmaceutically acceptable composition comprising a compound, to a subject in need thereof.

The term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

In certain embodiments, an "effective amount" of the compound or pharmaceutically acceptable composition is that amount effective in order to treat said disease. The compounds and compositions, according to the method of the present invention, may be administered using any amount and any route of administration effective for treating or lessening the severity of said disease.

In some embodiments, said disease is selected from a proliferative disorder, a neurodegenerative disorder, an autoimmune disorder, and inflammatory disorder, and an immunologically-mediated disorder. In some embodiments, said disease is selected from hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. In other embodiments, said disease is selected from hypercalcemia, osteoporosis, osteoarthritis, or symptomatic treatment of bone metastasis.

In yet other embodiments, said disease is a protein-kinase mediated condition. In some embodiments, said disease is an Src-mediated or Lck-mediated disease.

The term "protein kinase-mediated condition", as used herein, means any disease or other deleterious condition in which a protein kinase plays a role. Such conditions include, without limitation, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

The term "Src-mediated or Lck-mediated disease", as used herein means any disease or other deleterious condition in which Src or Lck is known to play a role. Accordingly, these compounds are useful for treating diseases or conditions that are affected by the activity of one or more Src-family kinases.

Such diseases or conditions include hypercalcemia, restenosis, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, cancer, Paget's disease, asthma, ischemic or reperfusion injury, allergic disease, atopic dermatitis, and allergic rhinitis. Diseases that are affected by Src activity, in particular, include hypercalcemia, osteoporosis, osteoarthritis, cancer, symptomatic treatment of bone metastasis, and Paget's disease. Diseases that are affected by Lck activity, in particular, include autoimmune diseases, allergies, rheumatoid arthritis, and leukemia.

In another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are another embodiment of the present invention. In some embodiments, said protein kinase-mediated condition is an Src-mediated or LCK-mediated condition.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a protein kinase-mediated condition (in some embodiments, an Src or LCK-mediated condition) comprising the step of administering to a patient one of the above-described pharmaceutical compositions.

In some embodiments, said method is used to treat or prevent a condition selected from hypercalcemia, osteoporosis, osteoarthritis, symptomatic treatment of bone metastasis, or any specific disease described above.

Another aspect of the invention relates to inhibiting protein kinase activity in a patient, which method comprises administering to the patient a compound of formula I, or a composition comprising said compound.

Depending upon the particular protein kinase-mediated conditions to be treated or prevented, additional drugs, which are normally administered to treat or prevent that condition, may be administered together with the inhibitors of this invention. For example, chemotherapeutic agents or other anti-proliferative agents may be combined with the protein kinase inhibitors of this invention to treat proliferative diseases.

Those additional agents may be administered separately, as part of a multiple dosage regimen, from the protein kinase inhibitor-containing compound or composition. Alternatively, those agents may be part of a single dosage form, mixed together with the protein kinase inhibitor in a single composition.

The compounds of this invention may be prepared in general by methods known to those skilled in the art. Those compounds may be analyzed by known methods, including but not limited to LCMS (liquid chromatography mass spectrometry) and NMR (nuclear magnetic resonance). Compounds of this invention may be also tested according to these examples. It should be understood that the specific conditions shown below are only examples, and are not meant to limit the scope of the conditions that can be used for making, analyzing, or testing the compounds of this invention. Instead, this invention also includes conditions known to those skilled in that art for making, analyzing, and testing the compounds of this invention.

EXAMPLES

As used herein, the term "Rt(min)" refers to the HPLC retention time, in minutes, associated with the compound. Unless otherwise indicated, the HPLC method utilized to obtain the reported retention time is as follows:

Column: ACE C8 column, 4.6×150 mm

Gradient: 0-100% acetonitrile+methanol 60:40 (20 mM Tris phosphate)

Flow rate: 1.5 mL/minute

Detection: 225 nm.

Mass spec. samples are analyzed on a MicroMass Quattro Micro mass spectrometer operated in single MS mode with electrospray ionization. Samples are introduced into the mass spectrometer using chromatography.

$^1$H-NMR spectra are recorded at 400 MHz using a Bruker DPX 400 instrument. The following compounds of formula I were prepared and analyzed as follows.

Intermediate 1

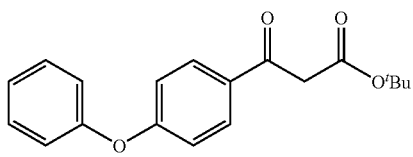

tert-Butyl 3-oxo-3-(4-phenoxyphenyl)propanoate

"Butyllithium (2.5 M, 7.9 ml, 19.76 mmol) was added at −20° C. to a solution of di-iso-propylamine (3.29 ml, 23.24 mmol) in tetrahydrofuran (40 ml). The reaction mixture was stirred for 15 minutes under nitrogen at −20° C. then the mixture was allowed to cool down to −78° C. tert-Butylacetate (2.64 ml, 19.67 mmol) was added and the mixture was stirred at −78° C. for 20 minutes. A solution of ethyl 4-phenoxybenzoate (2.17 g, 8.94 mmol) in tetrahydrofuran (5 ml) was further added to this and the resulting mixture was stirred at −78° C. for 50 minutes. A saturated solution of NH$_4$Cl was added and the whole was extracted with EtOAc. The organics were dried (MgSO$_4$), filtered and concentrated in vacuo. The residue was purified by silica gel chromatography eluting with 8% Et$_2$O in petroleum ether to afford the title compound as a colourless oil (1.53 g, 55% yield). MS (ES+) m/e=313. $^1$H NMR (CDCl$_3$) δH 1.47 (9H, s), 3.88 (2H, s), 7.02 (2H, d), 7.10 (2H, d), 7.24 (1H, t), 7.43 (2H, t), 7.94 (2H, d).

Intermediate 2

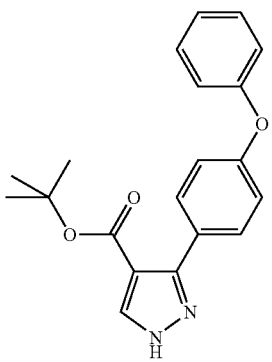

tert-Butyl 3-(4-phenoxyphenyl)-1H-pyrazole-4-carboxylate

To tert-Butyl 3-oxo-3-(4-phenoxyphenyl)propanoate (559 mg, 1.80 mmol) in tetrahydrofuran, was added Bredereck's reagent (1.18 mL, 5.70 mmol). The reaction mixture was stirred for 6 hours under nitrogen at reflux. The reaction mixture was concentrated in vacuo and taken up in EtOH (5 mL). Hydrazine monohydrate (79 μL, 1.63 mmol) was added and the reaction mixture was heated at reflux for 16 hours. The crude mixture was concentrated in vacuo, taken up in EtOAc, washed with water, a saturated aqueous solution of NaHCO$_3$ and brine. The organic phase was dried (MgSO$_4$), filtered and concentrated in vacuo. The residue was purified by silica gel chromatography (eluting with 40% EtOAc in petroleum ether) to afford the title compound (264 mg, 48% yield). MS (ES+) m/e=337. $^1$H NMR (CDCl$_3$) δH 1.52 (9H, s), 7.04 (2H, d), 7.06 (2H, d), 7.16 (1H, t), 7.38 (2H, t), 7.66 (2H, d), 7.95 (1H, s), 10.90 (1H, br s).

Intermediate 3

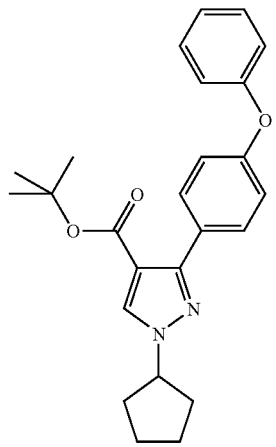

tert-Butyl 1-cyclopentyl-3-(4-phenoxyphenyl)-1H-pyrazole-4-carboxylate

To tert-Butyl 3-(4-phenoxyphenyl)-1H-pyrazole-4-carboxylate (156 mg, 0.46 mmol) in N,N-dimethylformamide (2 mL) was added sodium hydride, 60% in mineral oil (20.8 μg, 0.52 mmol). After the gas evolution ceased (about 5 minutes), cyclopentyl iodide (59 μL, 0.51 mmol) was added dropwise and the mixture was stirred for 16 hours at room temperature. EtOAc was added and the crude mixture was washed with a saturated aqueous solution of NaHCO$_3$. The aqueous phase was further extracted with EtOAc (3 times). The combined organic extracts were washed with water and brine. The organics were dried (MgSO$_4$), filtered and concentrated in vacuo. The residue was purified by silica gel chromatography (eluting with petroleum ether/DCM) to afford the title compound as a white solid (0.131 g, 69% yield). MS (ES+) m/e=405. $^1$H NMR (CDCl$_3$) δH 1.51 (9H, s), 1.70-1.80 (2H, m), 1.85-2.00 (2H, m), 2.02-2.13 (2H, m), 2.18-2.30 (2H, m), 4.71 (1H, quint.), 7.06 (4H, d), 7.12 (1H, t), 7.35 (2H, t), 7.76 (2H, d), 7.95 (1H, s).

Example 1

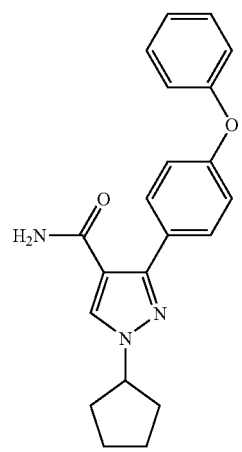

1-Cyclopentyl-3-(4-phenoxyphenyl)-1H-pyrazole-4-carboxamide I-2

Trifluoroacetic acid (5 mL) was added to a solution of tert-Butyl 1-cyclopentyl-3-(4-phenoxyphenyl)-1H-pyrazole- 4-carboxylate (129 mg, 0.32 mmol) in dichloromethane (5 mL). The reaction mixture was stirred at room temperature for 16 hours. The mixture was concentrated in vacuo and coevaporated 3 times with DCM.

The residue was dissolved in N,N-dimethylformamide (2 mL) and carbonyl diimidazole (88 mg, 0.54 mmol) was added. The reaction mixture was stirred at room temperature for 3 hours then, cooled down to 0° C. with an ice bath. Ammonia gas was bubbled into the solution for a few minutes and the mixture was stirred at room temperature for 40 minutes. Water was added and the white solid was filtered, rinsed with more water and dried. The residue was purified by reverse phase preparative HPLC [Waters Delta-Pak C18, 15 uM, 100 A column, gradient 10%-100% B (solvent A: 0.05% TFA in water; solvent B: $CH_3CN$) over 10 minutes at 25 mL/min] to afford the title compound as a white solid (88 mg, 79%) as a white solid. MS (ES+) m/e=348. $^1$H NMR ($CDCl_3$) δH 1.70-2.00 (4H, m), 2.00-2.12 (2H, m), 2.17-2.9 (2H, m), 4.71 (1H, quint.), 5.63 (2H, br s), 7.05-7.14 (4H, m), 7.18 (1H, t), 7.39 (2H, t), 7.60 (2H, d), 8.08 (1H, s).

Intermediate 4

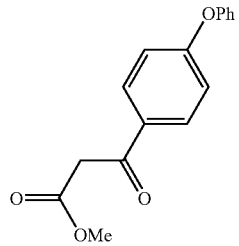

Methyl 3-oxo-3-(4-phenoxyphenyl)propanoate

In a three-necked flask equipped with a reflux condenser and stirbar under nitrogen was added 4'-phenoxyacetophenone (10 g, 47.1 mmol) in toluene (40 mL) dropwise at reflux to a suspension of sodium hydride (60% dispersion in mineral oil; 4.71 g, 0.12 mmol) in dimethylcarbonate (10.6 g, 0.12 mol) and toluene (20 mL). Ageing the reaction for 30 mins led to a solid mass to which was added acetic acid (5 mL) in water (25 mL). Added EtOAc (30 mL) and the organics were dried ($MgSO_4$), filtered and concentrated in vacuo. The residue was passed through a silica pad eluting with EtOAc/petroleum ether (3/20) and then concentrated. Petroleum ether was added and the less dense layer was decanted to give the ketoester (11.7 g, 92%) as a yellow oil, which solidified on standing. MS (ES+) m/e=271. $^1$H NMR: ($CDCl_3$) 3.87 (3H, s), 3.99 (2H, s), 7.02 (2H, d), 7.08 (2H, d), 7.25 (1H, t), 7.45 (2H, t), 7.94 (2H, d).

Intermediate 5

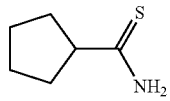

Cyclopentanecarbothioamide

Ammonia was bubbled through a solution of cyclopentanecarbonyl chloride (5.46 g, 41.1 mmol) in THF (60 mL) for 30 seconds. After 10 min, the ammonium chloride produced was filtered off and the filtrate concentrated. Then added EtOAc and water and separated the layers and re-extracted with a further portion of EtOAc. The combined organics were dried ($MgSO_4$), filtered and concentrated in vacuo to give the amide (4.46 g, 96%) as a clear oil. The amide (2.60 g, 23.0 mmol) from above was dissolved in THF (60 mL) and Lawesson's reagent (4.52 g, 11.18 mmol) was added under nitrogen. The mixture was heated at 70° C. After 90 min, toluene was added (30 mL) and heating continued overnight. Then the reaction mixture was concentrated and partitioned between EtOAc and water. The organic layer was concentrated and the residue purified by column chromatography (eluting with EtOAc/Pet ether, 1/1) to give the thioamide (2.44 g, 82%). $^1$H NMR: (DMSO) 1.45-1.88 (8H, m), 2.90 (1H, quin), 9.13 (1H, br s), 9.32 (1H, br s).

Intermediate 6

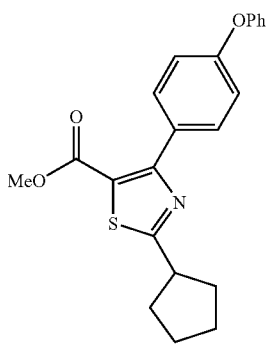

Methyl 2-cyclopentyl-4-(4-phenoxyphenyl)thiazole-5-carboxylate

To the ketoester (652 mg, 2.41 mmol) was added tetrabutyl ammonium tribromide (1.22 g, 2.53 mmol) at 0° C. in CH2Cl2 (20 mL). After 5 min the ice-bath was removed and the reaction was heated to reflux. After 3 h, the reaction was washed with sat. aq. $NaHCO_3$ and then concentrated. To this residue was added cyclopentanecarbothioamide (276 mg, 2.14 mmol) in ethanol (12 mL) and heated to 60° C. for 30 min. Concentrated the reaction and purified directly by column chromatography (eluting with EtOAc/Pet ether, 1/3) to give the thiazole (360 mg, 44%). MS (ES+) m/e=380. $^1$H NMR: ($CDCl_3$) 1.70-1.95 (6H, m), 2.20-2.29 (2H, m), 3.45-3.55 (1H, m), 7.05-7.09 (4H, m), 7.17 (1H, t), 7.39 (2H, t), 7.78 (2H, d).

Example 2

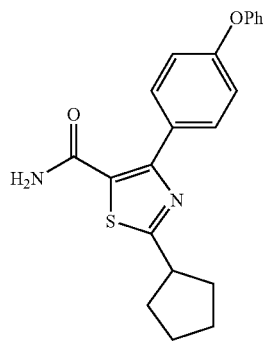

2-Cyclopentyl-4-(4-phenoxyphenyl)thiazole-5-carboxamide I-3

Methyl 2-cyclopentyl-4-(4-phenoxyphenyl)thiazole-5-carboxylate (265 mg, 0.70 mmol) was suspended in methanolic ammonia (7M, 10 mL) in a sealed vessel, which was then heated to 90° C. in an oil bath overnight. The reaction was then concentrated and purified by column chromatography (eluting with EtOAc/PE, 1/1) to give the aminothiazole (56 mg, 22%) as a white solid. MS (ES+) m/e=365. $^1$H NMR: (DMSO) 1.62-1.71 (2H, m), 1.72-1.85 (4H, m), 2.08-2.20 (2H, m), 3.46 (1H, quin), 7.02-7.10 (4H, m), 7.18 (1H, t), 7.42 (2H, t), 7.60-7.78 (4H, m).

Compound I-4 was prepared similarly to compound I-3 except substituting a cyclohexyl group for the cyclopentyl group.

Compound I-1 was found to inhibit Src at a $K_i$ value of 100 nM-500 nM. Compounds I-2, I-3, and I-4 were found to inhibit Src at a $K_i$ value of >1 μM.

Example 4

The compounds are evaluated as inhibitors of human Lck kinase using a spectrophotometric assay.

Lck Inhibition Assay

An assay buffer solution was prepared which consisted of 25 mM HEPES (pH 7.5), 10 mM MgCl$_2$, 250 μM NADH, 3

Analytical Data

| Cmpd | LCMS M+ | NMR_RESULT | HPLC Rt/Min |
|---|---|---|---|
| I-1 | 348.30 | $^1$H (DMSO) 1.61-1.72 (2H, m), 1.74-1.89 (4H, m), 2.03-2.12 (2H, m), 3.24 (1H, quintet), 7.07-7.11 (4H, m), 7.20 (1H, t), 7.32 (1H, bs), 7.41-7.47 (3H, m), 7.77 (2H, d). | 9.20 |
| I-2 | 348.30 | $^1$H (CDCl3) 1.70-2.00 (4H, m), 2.00-2.12 (2H, m), 2.17-2.9 (2H, m), 4.71 (1H, quint.), 5.63 (2H, br s), 7.05-7.14 (4H, m), 7.18 (1H, t), 7.39 (2H, t), 7.60 (2H, d), 8.08 (1H, s) | 9.612 |
| I-3 | 365.23 | $^1$H (DMSO) 1.62-1.71 (2H, m), 1.72-1.85 (4H, m), 2.08-2.20 (2H, m), 3.46 (1H, quin), 7.02-7.10 (4H, m), 7.18 (1H, t), 7.42 (2H, t), 7.60-7.78 (4H, m). | 9.75 |
| I-4 | 379.00 | $^1$H (DMSO) 1.11-1.59 95H, m), 1.63-1.86 (3H, m), 2.04-2.13 (2H, m), 2.96-3.06 (1H, m), 7.01-7.10 (4H, m), 7.15-7.21 (1H, m), 7.38-7.48 (2H, m), 7.58-7.79 (4H, m). | 10.39 |

Example 3

The compounds are evaluated as inhibitors of human Src kinase using a spectrophotometric assay.

Src Inhibition Assay

An assay buffer solution was prepared which consisted of 25 mM HEPES (pH 7.5), 10 mM MgCl$_2$, 250 μM NADH, 3 mM phosphoenolpyruvate, 60 μg/mL pyruvate kinase, 21 μg/mL lactate dehydrogenase, 113 μM ATP and 28 nM Src. To 60 μL of this solution, in a 96 well plate, was added 2 μL of test compound stock solution in DMSO and the mixture allowed to equilibrate for 10 mins at 30° C. The enzyme reaction was initiated by the addition of 5 μL 10 mg/mL poly Glu, Tyr (4:1) prepared in 25 mM HEPES (pH 7.5). Final assay concentrations of Src and ATP were 25 nM and 100 μM respectively. Initial rate data was determined from the rate of change of absorbance at 340 nM (corresponding to stoichiometric consumption of NADH) using a Molecular Devices Spectramax plate reader (Sunnyvale, Calif.) over 10 mins at 30° C. For each Ki determination 8 data points covering the test compound concentration range of 0-7.5 μM were obtained in duplicate. Ki values were calculated from initial rate data by non-linear regression using the Prism software package (Prism 4.0a, Graphpad Software, San Diego, Calif.).

mM phosphoenolpyruvate, 43 μg/mL pyruvate kinase, 14 μg/mL lactate dehydrogenase, 560 μM ATP and 67 nM Lck. To 60 μL of this solution, in a 96 well plate, was added 2 μL of test compound stock solution in DMSO and the mixture allowed to equilibrate for 10 minutes at 30° C. The enzyme reaction was initiated by the addition of 5 μL 15 mg/mL poly Glu, Tyr (4:1) prepared in 25 mM HEPES (pH 7.5). Final assay concentrations of Lck and ATP are 60 nM and 500 μM respectively. Initial rate data was determined from the rate of change of absorbance at 340 nM (corresponding to stoichiometric consumption of NADH) using a Molecular Devices Spectramax plate reader (Sunnyvale, Calif.) over 10 min at 30° C. For each Ki determination 8 data points covering the test compound concentration range of 0-7.5 μM are obtained in duplicate. Ki values are calculated from initial rate data by non-linear regression using the Prism software package (Prism 4.0a, Graphpad Software, San Diego, Calif.).

Compounds of this invention were found to inhibit Lck at a $K_i$ value of <1 μM. More specifically, compound I-1 was found to inhibit Lck at a $K_i$ value of <100 nM. Compound I-2 and compound I-3 were found to inhibit Lck at a $K_i$ value of 100 nM-500 nM. Compound I-4 is expected to inhibit Lck at a $K_i$ value of <1 μM (based on assay results in view of the relatively low solubility of 1-4 under the assay conditions).

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:
1. A compound of formula I:

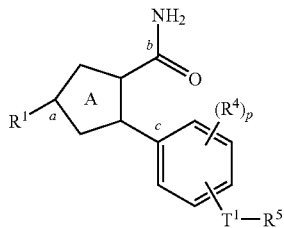

or a pharmaceutically acceptable salt thereof;
wherein
$R^1$ is a 3-7 membered monocyclic cycloalkyl optionally substituted with 0-4 $J^1$;
Ring

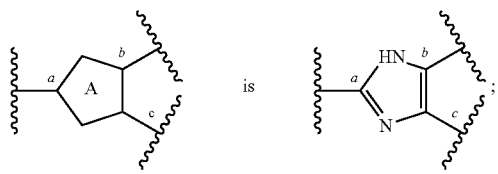

$R^4$ is H, $C_{1-6}$aliphatic, $C_{3-6}$cycloaliphatic, halo($C_{1-4}$ aliphatic), 3-8 membered heterocyclyl, halo, $NO_2$, CN, OH, OR'', SH, SR'', $NH_2$, NHR'', NR''$_2$, COH, COR'', $CO_2H$, $CO_2R''$, $CONH_2$, CONHR'', CONR''$_2$, OC(O)R'', OC(O)NH$_2$, OC(O)N(H)R'', OC(O)NR''$_2$, N(H)C(O)R'', N(R'')C(O)R'', N(H)CO$_2$R'', N(R'')CO$_2$R'', N(H)CO$_2$H, N(R'')CO$_2$H, N(H)CONH$_2$, N(H)C(O)N(H)R'', N(H)CONR''$_2$, SO$_2$NH$_2$, SO$_2$N(H)R'', SO$_2$NR''$_2$, N(H)SO$_2$R'', N(R'')SO$_2$R'', P(O)R'$_2$, PO$_2$R', P(O)R'$_2$, or P(O)(OR')$_2$;
R'' is unsubstituted $C_{1-6}$aliphatic or $C_{1-4}$haloaliphatic; or two R'' groups, together with the atom to which they are bound, form an unsubstituted 3-8 membered nonaromatic monocyclic ring consisting of 0-1 heteroatoms independently selected from O, N, and S;
$T^1$ is a $C_{1-6}$ aliphatic chain wherein 0-3 methylene units of the chain are optionally replaced with —N(R)—, —O—, —S—, —C(O)—, —C(=NR)—, —C(=NOR)—, —SO—, or —SO$_2$—; each $T^1$ is optionally substituted with 0-2 $J^T$;
$R^5$ is a 5-10 membered aromatic ring consisting of 0-4 heteroatoms selected from O, N, and S; each $R^5$ is optionally substituted with 0-5 $J^5$;
$J^5$ is H, $C_{1-6}$aliphatic, $C_{3-8}$cycloaliphatic, halo($C_{1-4}$ aliphatic), 3-8 membered heterocyclyl, halo, $NO_2$, CN, OH, OR', SH, SR', $NH_2$, N(H)R', NR'$_2$, C(O)H, C(O)R', CO$_2$H, CO$_2$R', C(O)NH$_2$, C(O)N(H)R', C(O)NR'$_2$, OC(O)R', OC(O)NH$_2$, OC(O)NHR', OC(O)N(R')$_2$, N(H)C(O)R', N(R')C(O)R', N(H)CO$_2$R', N(R')CO$_2$R', N(H)CO$_2$H, N(R')CO$_2$H, N(H)CONH$_2$, N(H)C(O)NHR', N(H)CON(R')$_2$, SO$_2$NH$_2$, SO$_2$NHR', SO$_2$NR'$_2$, N(H)SO$_2$R', N(R')SO$_2$R', P(O)R', PO$_2$R', P(O)R'$_2$, or P(O)OR'$_2$;
R is H or unsubstituted $C_{1-6}$aliphatic;
R' is unsubstituted $C_{1-6}$aliphatic or $C_{1-4}$ haloaliphatic; or two R' groups, together with the atom to which they are bound, form an unsubstituted 3-8 membered nonaromatic monocyclic ring consisting of 0-1 heteroatoms independently selected from O, N, and S;
$J^1$ is $M^1$ or —$Y^1$-$M^1$;
each $Y^1$ is independently an unsubstituted $C_{1-6}$aliphatic optionally replaced with 0-3 occurrences of —N(R)—, —O—, —S—, —C(O)—, —SO—, or —SO$_2$—;
each $M^1$ is independently H, $C_{1-6}$aliphatic, $C_{3-8}$cycloaliphatic, halo($C_{1-4}$ aliphatic), —O(halo$C_{1-4}$ aliphatic), 3-8 membered heterocyclyl, 5-6 membered heteroaryl, phenyl, halo, NO$_2$, CN, OH, OR', SH, SR', NH$_2$, N(H)R', NR'$_2$, C(O)H, C(O)R', CO$_2$H, CO$_2$R', C(O)NH$_2$, C(O)NHR', C(O)NR'$_2$, OC(O)R', OC(O)NH$_2$, OC(O)NHR', OC(O)N(R')$_2$, N(H)C(O)R', N(R')C(O)R', N(H)CO$_2$R', N(R')CO$_2$R', N(H)CO$_2$H, N(R')CO$_2$H, N(H)C(O)NH$_2$, N(H)C(O)N(H)R', N(H)C(O)NR'$_2$, SO$_2$NH$_2$, SO$_2$NHR', SO$_2$N(R')$_2$, NHSO$_2$R', NR'SO$_2$R', P(O)R', PO$_2$R', P(O)R'$_2$, or P(OOR'$_2$;
each $R^4$, $J^5$, and $M^1$ is independently and optionally substituted with 0-5 J;
each $J^T$ and J is independently H, halo, $C_{1-6}$ aliphatic, $C_{3-6}$cycloaliphatic, NO$_2$, CN, —NH$_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), CONH$_2$, CONH($C_{1-4}$ aliphatic), CON($C_{1-4}$ aliphatic)$_2$, —CO$_2$H, —CO$_2$($C_{1-4}$ aliphatic), —O(halo$C_{1-4}$ aliphatic), or halo($C_{1-4}$ aliphatic);
p is 0-4.
2. The compound according to claim 1, wherein $T^1$-$R^5$ is bonded in the para position (relative to bond c) as shown in formula II:

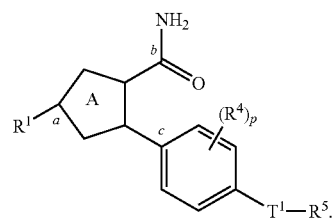

3. The compound according to claim 1, wherein $R^1$ is a 5 or 6 membered cycloalkyl ring.
4. The compound according to any one of claims 1-3, wherein $R^4$ is H, halo, $C_{1-6}$ aliphatic, $C_{3-6}$cycloaliphatic, NO$_2$, CN, —NH$_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), CONH$_2$, CONH($C_{1-4}$ aliphatic), CON($C_{1-4}$ aliphatic)$_2$, —CO$_2$H, —C$_2$($C_{1-4}$ aliphatic), —O(halo$C_{1-4}$ aliphatic), or halo($C_{1-4}$ aliphatic).
5. The compound according to claim 4, wherein $T^1$ is O, N, S, —C(O)N(R)— or —N(R)C(O)—.
6. The compound according to claim 5, wherein $T^1$ is O.
7. The compound according to claim 5, wherein R is H.
8. The compound according to any one of claims 1-3, wherein $R^5$ is an optionally substituted indole.
9. The compound according to any one of claims 1-3, wherein $R^5$ is an optionally substituted 6-membered aryl or heteroaryl ring.
10. The compound according to claim 9, wherein $R^5$ is optionally substituted phenyl.

11. The compound according to claim 10, wherein $J^5$ is H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), CONH$_2$, CONH($C_{1-4}$ aliphatic), CON($C_{1-4}$ aliphatic)$_2$, —CO$_2$H, —CO$_2$($C_{1-4}$ aliphatic), —O(halo$C_{1-4}$ aliphatic), or halo($C_{1-4}$ aliphatic).

12. The compound according to claim 1, wherein the compound has one or more of the following variable definitions:
   a) Ring

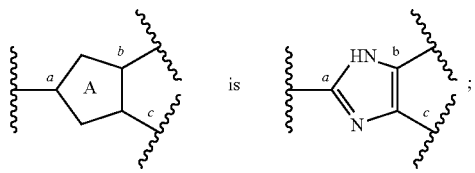

b) $T^1$ is O;
   c) $R^5$ is optionally substituted phenyl; and
   d) $R^4$ is H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), CONH$_2$, CONH($C_{1-4}$ aliphatic), CON($C_{1-4}$ aliphatic)$_2$, —CO$_2$H, —CO$_2$($C_{1-4}$ aliphatic), —O(halo$C_{1-4}$ aliphatic), or halo($C_{1-4}$ aliphatic).

13. The compound according to claim 12, wherein the compound has the following variable definition:
   a) Ring

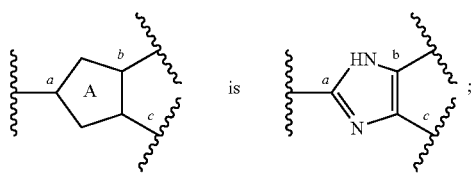

b) $T^1$ is O;
   c) $R^5$ is optionally substituted phenyl; and
   d) $R^4$ is H, halo, $C_{1-6}$ aliphatic, $C_{3-6}$cycloaliphatic, $NO_2$, CN, —$NH_2$, —NH($C_{1-4}$ aliphatic), —N($C_{1-4}$ aliphatic)$_2$, —OH, —O($C_{1-4}$ aliphatic), COH, —CO($C_{1-4}$ aliphatic), CONH$_2$, CONH($C_{1-4}$ aliphatic), CON($C_{1-4}$ aliphatic)$_2$, —CO$_2$H, —CO$_2$($C_{1-4}$ aliphatic), —O(halo$C_{1-4}$ aliphatic), or halo($C_{1-4}$ aliphatic).

14. The compound according to claim 1, wherein the compound is represented by the following structural formula:

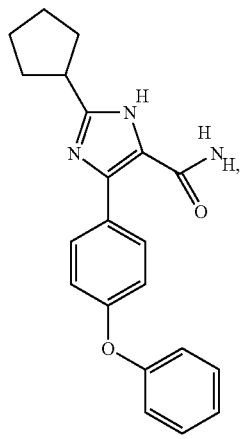

or a pharmaceutically acceptable salt thereof.

15. A composition comprising a compound according to claim 1, and a pharmaceutically acceptable carrier, adjuvant, or vehicle.

16. A composition for coating an implantable device comprising a compound according to claim 1 and a carrier suitable for coating said implantable device.

17. A process for preparing a compound of formula I:

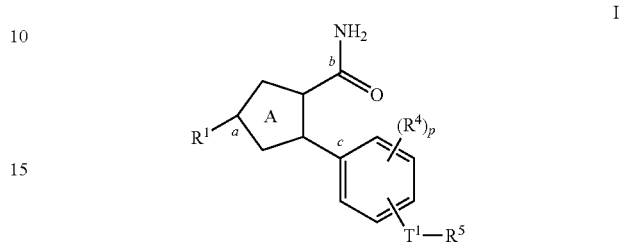

wherein ring

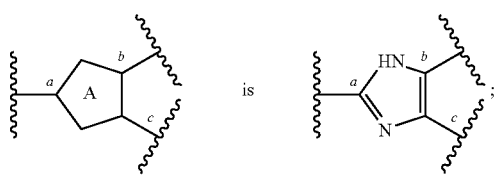

and $R^1$, $R^4$, $T^1$, $R^5$, and p are defined according to claim 1; comprising
   reacting a compound of formula 4;

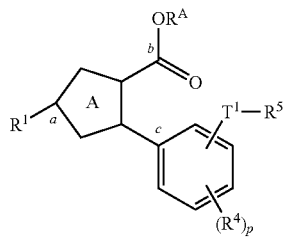

wherein Ring A, $R^1$, $R^4$, $T^1$, $R^5$, and p are defined according to claim 1 and $R^A$ is H or $C_{1-6}$alkyl;
      under suitable amide-formation conditions to form the compound of formula I.

18. The process of claim 17, further comprising the steps of:
   (a) reacting a compound of formula 2-b;

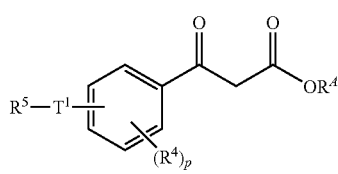

wherein; and $R^A$ is $C_{1-6}$alkyl;
      under suitable oxidizing conditions to form a compound of formula 3-b:

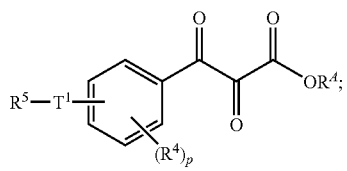

wherein; and $R^A$ is $C_{1-6}$alkyl;

(b) cyclizing the compound of formula 3-b with $R^1$CHO under suitable cyclization conditions to form a compound of formula 4, wherein ring

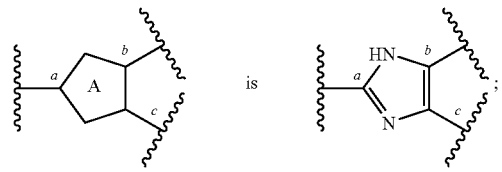

$R^A$ is $C_{1-6}$alkyl.

19. The process of claim 18, further comprising the step of reacting a compound of formula 1-b:

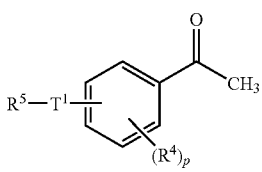

wherein;
with a suitable base and diethylcarbonate under suitable conditions; to form a compound of formula 2-b:

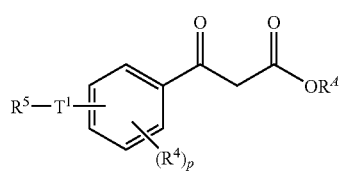

wherein; and $R^A$ is $C_{1-6}$alkyl.

* * * * *